United States Patent [19]

Kushlefsky

[11] 4,058,544
[45] Nov. 15, 1977

[54] NOVEL METHOD FOR PREPARING ORGANOTIN COMPOUNDS

[75] Inventor: Bernard G. Kushlefsky, Edison, N.J.

[73] Assignee: M&T Chemicals Inc., Greenwich, Conn.

[21] Appl. No.: 530,356

[22] Filed: Dec. 6, 1974

[51] Int. Cl.$^2$ .............................................. C07F 7/22
[52] U.S. Cl. .................................................. 260/429.7
[58] Field of Search ...................................... 260/429.7

[56] References Cited

U.S. PATENT DOCUMENTS

| | | | |
|---|---|---|---|
| 2,838,554 | 6/1958 | Gloskey | 260/429.7 |
| 3,016,369 | 1/1962 | Montermoso et al. | 260/429.7 |
| 3,167,532 | 1/1965 | Leebrick | 260/429.7 X |
| 3,257,194 | 6/1966 | Miller | 260/429.7 X |
| 3,555,148 | 1/1971 | Katsumura et al. | 260/429.7 X |

OTHER PUBLICATIONS

Anderson, J. Org. Chem., v. 22, pp. 147–148 (1957).
Montermoso et al., J. Polymer Science, v. 32, pp. 523–525 (1958).
Shostakovski et al., J. Polymer Science, v. 52, pp. 223–229 (1961).
Matwiijoff et al., J. Organometal. Chem. 3, pp. 393–399 (1965).
Chemical Abstracts, v. 52, 16201e (1958).
Luijten et al., Investigations in the Field of Organotin Chemistry, England, pp. 104, 105, 107, 109 (1955).

*Primary Examiner*—Helen M. S. Sneed
*Attorney, Agent, or Firm*—Robert P. Auber; Kenneth G. Wheeless; Robert Spector

[57] ABSTRACT

Triorganotin derivatives of polymerizable ethylenically unsaturated carboxylic acids are prepared either in the presence or absence of solvent by reacting the acid or a suitable derivative thereof with a triorganotin hydroxide or a bis(triorganotin)oxide. Polymerization of the acid or the triorganotin derivative thereof is avoided by using a dehydrating agent to remove the water formed as a by-product of the reaction.

7 Claims, No Drawings

NOVEL METHOD FOR PREPARING ORGANOTIN COMPOUNDS

BACKGROUND

This invention relates to the preparation of triorganotin compounds. This invention further relates to the preparation of polymerizable triorganotin derivatives of unsaturated carboxylic acids.

Polymers derived from triorganotin derivatives of unsaturated monocarboxylic acids, particularly acrylic and methacrylic acids, have been recognized as effective toxicants for numerous applications, including antifouling paints. The use of these polymers for protecting a variety of materials against the growth of harmful organisms is disclosed in U.S. Pat. No. 3,167,473.

Monomeric precursors of the aforementioned polymers are prepared by reacting an ethylenically unsaturated acid, such as acrylic acid, or a suitable derivative thereof, such as the corresponding acid anhydride, with a triorganotin hydroxide or a bis(triorganotin)oxide. The water formed as a by-product of the reaction is conventionally removed by distillation which is conducted under either atmospheric or reduced pressure. The reaction of an acid with a triorganotin hydroxide can be expressed by the following equation:

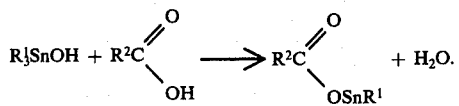

In the foregoing equation $R^1$ represents a hydrocarbon radical containing between 1 and 20 carbon atoms and $R^2$ represents an ethylenically unsaturated hydrocarbon radical.

The reaction mixture usually includes an inert liquid diluent such as an aromatic hydrocarbon, which forms an azeotropic mixture with water. The acid and triorganotin compound are usually heated to the boiling point of the reaction mixture and a distillation apparatus is employed to remove the water together with a portion of the hydrocarbon diluent. In addition to facilitating removal of the relatively small amount of water formed during the reaction, the diluent lowers the concentration of unsaturated acid and the triorganotin derivative thereof, thereby reducing the likelihood of a spontaneous polymerization. This type of polymerization is undesirable in those instances when the organotin derivative is to be subsequently reacted with other ethylenically unsaturated compounds to form copolymers such as those disclosed in U.S. Pat. No. 3,167,473.

The distillation of hydrocarbon diluent and water is often conducted under reduced pressure to minimize heating of the reaction mixture.

The use of an organic diluent and distillation to remove the diluent and by-product water may be satisfactory when the total volume of reagents and diluent does not exceed about 500 c.c. As the volume of the reaction mixture increases, it becomes more difficult to evenly distribute heat from the walls of the reactor throughout the reaction mixture. Localized overheating may occur, particularly in areas adjacent to that portion of the reaction vessel where heat is being applied. The heat input required to maintain a distillation wherein the vapor phase remains at ambient temperature is significant. If the heat is not rapidly dissipated within the reaction mixture, the resultant localized overheating could initiate a spontaneous polymerization.

An objective of this invention is to provide a method for preparing relatively large amounts of triorganotin carboxylates derived from ethylenically unsaturated acids with or without any organic diluent and in the absence of significant polymer formation.

It has now been found that this objective can be realized by replacing the conventional distillation step for the removal of water by the use of certain chemicals which will effectively remove the water from the liquid phase of the reaction mixture.

SUMMARY OF THE INVENTION

This invention provides an improvement in the method for preparing triorganotin derivatives of ethylenically unsaturated acids by (1) reacting an ethylenically unsaturated mono- or dicarboxylic acid or suitable derivative therof with a triorganotin hydroxide or bis(triorganotin)oxide and (2) removing the water formed as a by-product of said reaction. The reaction mixture may optionally include a liquid diluent. The improvement provided by this invention resides in removing the by-product water by maintaining the reaction mixture in contact with an amount of a chemically inert dehydrating agent sufficient to remove substantially all of the water. The reaction mixture is maintained in contact with the dehydrating agent for a period of time sufficient to the dehydrating agent to react with or absorb between 95 and 100% of the water present.

DETAILED DESCRIPTION OF THE INVENTION

The present class of dehydrating agents include anhydrous salts which react with water to form stable hydrates or particulate materials such as activated aluminum and molecular sieves that are insoluble in the reaction mixture and selectively absorb water on the surface of the particles, within the particles or both. Preferred salts yielding stable hydrates include the anhydrous forms of magnesium sulfate, calcium sulfate, the calcium halides (fluoride, chloride, bromide and iodide), potassium carbonate and sodium sulfate. Other anhydrous salts are suitable if they are competitive in cost and performance with the preferred species and are chemically inert, in that they are not polymerization catalysts for the unsaturated acid and do not render the resultant reaction mixture so acidic or basic as to initiate a polymerization of the unsaturated acid or the triorganotin derivative thereof. Drying agents which are too acidic or basic can also decompose the organotin ester. It is this criterion of chemical inertness that excludes both alkali metal or alkaline earth metal hydroxides and phosphorus pentoxide from the class of useful dehydrating agents.

Preferred drying agents which remove water by absorption include activated alumina, silica gel and molecular sieves, particularly the types designated 4A and 5A.

The amount of dehydrating agent employed in the method of this invention is at least sufficient to remove between 95 and 100% of the theoretical amount of water formed during the reaction. The number of moles of water is equal to the number of equivalents of carboxylic acid reacted with the triorganotin compound. It is preferable to use between a 10 and 50% excess of dehydrating agent over this theoretical amount. Using any larger excess would add to the cost of the process without any significant corresponding increase in efficiency or rate of the dehydration step.

The reaction between the acid and the triorganotin compound can be conducted in any organic liquid wherein the reactants and product are soluble. It is often desirable to prepare the monomer in the solvent in which it will subsequently be polymerized. If the polymer is to be incorporated into a paint, it is often desirable to prepare the monomer in mineral spirits, a mixture of liquid hydrocarbons.

An unexpected advantage resulting from use of the present dehydrating agents is that triorganotin derivatives of unsaturated acids can be prepared without any solvent or diluent.

Heretofore, it has usually been necessary to include a liquid hydrocarbon that forms an azeotropic mixture with water in order to remove the water and dissipate the heat input required to effect a continuous distillation. The operability of the present method in the absence of a solvent makes it possible to decrease the volume of material required to react a given amount of acid with a triorganotin compound, thereby increasing volume efficiency and reducing processing costs. Moreover, certain organic liquids such as mineral spirits, in which it may be desired to subsequently polymerize the present triorganotin compounds, may be unsuitable for preparing the monomer using prior art methods requiring removal of water by distillation, since the hydrocarbon will not form an azeotropic mixture with water. In these instances the monomer must be separated from the solvent in which it is prepared and subsequently combined with the polymerization medium. Usually the aforementioned separation entails distilling the reaction mixture solvent. The prolonged heating required to effect such a distillation may initiate a spontaneous exothermic polymerization of the monomeric triorganotin compound.

In accordance with the method of this invention, one or more triorganotin derivatives of unsaturated mono- or polycarboxylic acids are combined with a stoichiometric amount of one or more triorganotin hydroxides of the formula $R_3^1SnOH$ or the corresponding bis(triorganotin)oxides of the formula $(R_3^1Sn)_2O$, wherein $R^1$ represents an alkyl radical containing between 1 and 20 carbon atoms, a cycloalkyl, aryl, alkaryl or an aralkyl radical. The reaction can optionally be conducted in the presence of a suitable organic solvent, as discussed hereinbefore. When the unsaturated acid is acrylic or methacrylic acid, the reaction between the acid and the triorganotin compound is often exothermic and may not require external heating. If desired the reaction vessel can be cooled by placing it in an ice-water mixture or other suitable low temperature environment to maintain the reacting mixture at a temperature of between 0° C. and ambient temperature. Cooling is considered optional, since neither the quality or yield of product were adversely affected when the temperature of the reaction mixture spontaneously rose to as high as 57° C. due to heat generated by the exothermic reaction.

The ethylenically unsaturated acid that is reacted with a triorganotin compound in accordance with the method of this invention is of the general formula $R^2(COOH)_n$ wherein $R^2$ is a monovalent or divalent hydrocarbon radical containing between 2 and 20 carbon atoms and a double bond between 2 adjacent carbon atoms that do not form part of an aromatic ring structure, such as a phenyl ring. The subscript $n$ represents the integer 1 or 2, and is also equal to the valence of $R^2$. In a preferred embodiment of the present method $n$ is 1, i.e., the acid is a monocarboxylic acid, and $R^2$ is a radical of the formula $H_2C=CH-$ or $H_2C=C(CH_3)-$, which corresponds to acrylic acid and methacrylic acid, respectively. Other suitable ethylenically unsaturated monocarboxylic acids include crotonic, isocrotonic, 3-butenoic, oleic, 1-cyclohexene-1-carboxylic, and cinnamic acids, in addition to unsaturated acids such as abietic acid that are extracted from rosin and other natural products.

Dicarboxylic acids containing ethylenic unsaturation include maleic, fumaric, citraconic, itaconic and the isomeric tetrahydrophthalic acids, among others.

The reaction between the triorganotin compound and unsaturated acids other than acrylic, methacrylic, maleic or fumaric acids may be relatively slow, particularly if the acid is sterically hindered. In these instances it may be necessary to heat the mixture slightly, i.e., to a temperature between 30° and 50° C., to achieve a useful reaction rate while avoiding polymerization of the unsaturated acid.

Using the preferred acrylic or methacrylic acid, the reaction with the triorganotin compound is substantially complete after only several minutes at ambient temperature. The yield of desired product is usually greater than 90% of the theoretical value.

The triorganotin reagent employed in the method of this invention is a triorganotin hydroxide or a bis(triorganotin)oxide wherein the three hydrocarbon radicals bonded to the tin atom contain between 1 and 20 carbon atoms. The radicals can be alkyl, cycloalkyl, aryl, alkaryl or aralkyl. If the polymer which is ultimately prepared from the monomeric products of the present method is to be employed to control undesirable organisms as taught in U.S. Pat. No. 3,167,473, the radicals represented by $R^1$ are preferably propyl, butyl, cyclohexyl or phenyl radicals. The choice of radicals for $R^1$ will be in large measure determined by the desired end use for the ultimate polymer.

Polymers wherein the $R^1$ radicals are other than propyl, butyl, cyclohexyl or phenyl are useful in numerous applications, including catalysts for many types of reactions, antioxidants for rubber, and as additives for oils and other products.

The three $R^1$ radicals are preferably identical, but need not be so. Synthetic methods for preparing both symmetrically and asymmetrically substituted triorganotin oxides and hydroxides are sufficiently disclosed in the chemical and patent literature that a detailed discussion of this subject is not required as part of the present specification.

The dehydrating agent is preferably added following completion of the reaction between the unsaturated acid and the triorganotin compound. If the dehydrating agent is present during this reaction, product yield may be decreased due to adsorption or absorption of the reagents by the solid dehydrating agent. The contact time between the drying agent and reaction mixture should be at least several minutes to ensure that most, if not all, of the water reacts with or is adsorbed by the dehydrating agent. Agitating the mixture of dehydrating agent and reaction product together with a liquid organic diluent, if present, is desirable since this maximizes the area of contact between the solid dehydrating agent and the liquid reaction mixture, thereby accelerating the rate at which water is removed from the liquid phase by the dehydrating agent.

The following examples disclose preferred embodiments of the present invention and should not be regarded as limiting the scope of the method defined in the accompanying claims. All parts and percentages are by weight.

EXAMPLE 1

This example demonstrates the effect of reaction temperature on the yield of tributyltin methacrylate prepared using the method of this invention.

A. An 86.1 g. portion of methacrylic acid containing 100 parts per million of p-methoxy phenol as a polymerization inhibitor was gradually added over a 10 minute period to 289 g. of bis-tri-n-butyltin oxide (TBTO). Prior to addition of the acid, the TBTO was cooled to 5° C. by immersing the reaction vessel in an ice-water mixture. The reaction mixture was stirred and cooled during addition of the acid, and the temperature of the reaction mixture increased to 20° C. Stirring was continued for five minutes following completion of the acid addition, at which time 25 g. of anhydrous magnesium sulfate were added to the reaction mixture. The resultant two phase mixture was stirred for 10 minutes and filtered to separate the solid and liquid phases. The latter was a slightly off-white mobile oil equivalent to a 90% yield, based on TBTO. It was assumed that additional product was entrapped by the solid phase.

A potentiometric titration of the reaction product revealed no free TBTO and 0.65% of free methacrylic acid. The product was found to contain 0.33% water, as determined by Karl Fisher analysis, and 31.2% tin (calculated tin content for tri-n-butyltin methacrylate = 31.7%). The acid number of the product was 148 (calculated value = 149.5). The product dissolved in methanol to yield a clear solution, indicating that no polymer was present.

B. The procedure described in part A of this example was repeated using the same amounts of TBTO and methacrylic acid. The temperature of the reaction mixture was allowed to reach a maximum of 28° C. during the addition of the methacrylic acid, following which 20 g. of anhydrous magnesium sulfate were added. After being stirred for 30 minutes, the liquid phase was separated from the resultant mixture to yield 353.4 g. (94.2% yield) of an off-white oil that upon analysis was found to contain 31.05% tin, 0.35% water, 0.90% free methacrylic acid and no free TBTO. The acid number of the product was 148.57.

C. Tributyltin methacrylate was prepared using the general procedure described in part A of this example using twice the amounts of TBTO and methacrylic acid specified in part A. The reaction vessel was not cooled either prior to or during the addition of methacrylic acid, which was added in two portions of approximately 100 cc. each. The temperature of the reaction mixture increased to 49° C. following addition of the first portion of acid and reached a maximum of 57° C. during addition of the second portion. A 40 g. portion of anhydrous magnesium sulfate was then added, the resultant two-phase mixture stirred for 1 hour and the solid phase removed by filtration to yield 723 g. (96.4% yield) of an off-white oil which was completely miscible with methanol. The reaction product contained 30.2% tin, 0.21% water and no free TBTO or methacrylic acid. The acid number of the product was 152.6.

EXAMPLE 2

This example demonstrates the use of anhydrous calcium sulfate. Although this salt does not have the same water capacity for a given weight as anhydrous magnesium sulfate, it is more effective in reducing the water content of the product.

A. A 172.2 g. portion of methacrylic acid was gradually added over a five minute period, with stirring, to 596 g. of TBTO which had been cooled to 10° C. The temperature of the reaction mixture increased to 36° C. during the addition of the acid. When the addition was completed, 20 g. of anhydrous magnesium sulfate were added and stirring continued for 15 minutes. The mobile oil obtained following separation of the solid phase weighed 737.7 g. (equivalent to a yield of 98.3%, based on TBTO) and contained 0.75% water. The relatively high water content indicated that 20 g. of anhydrous magnesium sulfate was insufficient to absorb all of the water present in the tributyltin methacrylate. When this product was combined with 20 g. of anhydrous calcium sulfate and the mixture stirred for 30 minutes, the water content was reduced to 0.44%.

B. A reaction vessel equipped with a thermometer, nitrogen inlet, agitator and condenser was charged with 225 g. of mineral spirits and 596 g. of TBTO. The solution was purged with nitrogen for 15 minutes following which 17.0 cc. of methacrylic acid were added dropwise over a 30 minute period, during which time the temperature rose from 23° C to 27° C.

The cloudy reaction mixture was then agitated for an additional 30 minutes after which 9 g. of anhydrous magnesium sulfate was added. After agitating for an additional 30 minutes, the mixture was filtered.

The liquid phase weighed 289 g. and was found to contain 0.2% water. An aliquot of the solution was then stirred with 10 g. of anhydrous calcium sulfate for 2 hours, refiltered and analyzed for water content.

Found — 0.02% water
%Free TBTO — none found
%Free Methacrylic Acid — none found

EXAMPLE 3

This example illustrates the problems that can occur when triorganotin derivatives of unsaturated acids are prepared using a prior art method.

A reaction vessel was charged with 5961 g. (10 moles) of TBTO, 1722 g. (20 moles) of methacrylic acid containing 100 parts per million of p-methoxy phenol as a polymerization inhibitor, and 8 liters of heptane. The contents of the reaction vessel were stirred while under a partial vacuum (39–65 mm. of mercury) to remove the water formed as a by-product of the reaction. An azeotropic mixture of water and heptane was collected in a trap which permitted return of the heptane to the reaction vessel. The contents of the vessel were heated to maintain the liquid phase at a temperature of 34° C. throughout the distillation, which was continued until the theoretical amount of water collected in the trap. The solution in the reaction vessel was miscible with methanol to yield a clear solution, indicative of no oligomer or polymer formation. An attempt to separate the tributyltin methacrylate from the heptane by distillation yielded a rubbery polymer, even though the temperature of the mixture did not exceed 23° C. during the distillation.

What is claimed is:

1. In an improved method for preparing a triorganotin derivative of an ethylenically unsaturated mono- or dicarboxylic acid containing between 3 and 20 atoms, the method consisting essentially of
   1. reacting said mono- or dicarboxylic acid with a stoichiometric amount of a triorganotin hydroxide or a bis(triorganotin)oxide;
   2. removing the water formed as a by-product of the reaction from the reaction mixture; and
   3. isolating said triorganotin derivative, wherein the improvement resides in removing the water by maintaining the triorganotin derivative in contact with an amount of a solid, chemically inert dehydrating agent sufficient to remove all of the water present in the reaction mixture, and separating said triorganotin derivative from the dehydrating agent, said dehydrating agent being selected from the group consisting of the anhydrous forms of sodium sulfate, magnesium sulfate, calcium sulfate, the calcium halides, activated alumina, silica gel and molecular sieves.

2. An improved method as described in claim 1 wherein the triorganotin hydroxide exhibits the formula $R_3^1SnOH$ and the bis(triorganotin)oxide exhibits the formula $(R_3^1Sn)_2O$, wherein each $R^1$ is individually selected from the group consisting of alkyl radicals containing between 1 and 20 carbon atoms, inclusive, cycloalkyl, aryl, alkaryl and aralkyl radicals.

3. An improved method as described in claim 1 wherein the ethylenically unsaturated carboxylic acid exhibits the formula $R^2$

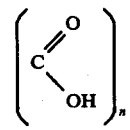

wherein $R^2$ represents a hydrocarbon radical with a valence of $n$ and containing from 2 to 20 carbon atoms inclusive, and a double bond between 2 adjacent carbon atoms that do not form part of an aromatic ring structure, and $n$ is 1 or 2.

4. An improved method as described in claim 3 wherein $n$ is 1 and $R^2$ represents the radical

5. An improved method as described in claim 1 wherein the bis(triorganotin)oxide is bis(tri-n-butyltin)oxide.

6. An improved method as described in claim 1 wherein the reaction between the ethylenically unsaturated acid and triorganotin hydroxide or bis(triorganotin)oxide is conducted in the absence of a solvent or diluent.

7. An improved method as described in claim 1 wherein the reaction between the ethylenically unsaturated acid and the triorganotin hydroxide or bis(triorganotin)oxide is conducted in the presence of a liquid hydrocarbon wherein both the reactants and the product are soluble.

* * * * *